(12) United States Patent
Fowler et al.

(10) Patent No.: US 9,393,076 B2
(45) Date of Patent: Jul. 19, 2016

(54) INSERTABLE DEVICE AND SYSTEM FOR MINIMAL ACCESS PROCEDURE

(71) Applicant: THE TRUSTEES OF COLUMBIA UNIVERSITY IN THE CITY OF NEW YORK, New York, NY (US)

(72) Inventors: Dennis L. Fowler, Boston, MA (US); Peter K. Allen, Pleasantville, NY (US); Andrew T. Miller, Brooklyn, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/073,483

(22) Filed: Nov. 6, 2013

(65) Prior Publication Data
US 2014/0066954 A1 Mar. 6, 2014

Related U.S. Application Data

(60) Division of application No. 11/475,737, filed on Jun. 26, 2006, now abandoned, which is a continuation of application No. 11/226,665, filed on Sep. 13, 2005, now abandoned, which is a continuation-in-part of application No. 10/620,298, filed on Jul. 15, 2003, now Pat. No. 7,066,879, application No. 14/073,483, which is a continuation of application No. 12/066,559, filed as application No. PCT/US2006/035858 on Sep. 13, 2006, now abandoned, which is a continuation of application No. 11/226,665, which is a continuation-in-part of application No. 10/620,298, application No. 14/073,483, which is a continuation-in-part of application No. 12/770,246, filed as application No. PCT/
(Continued)

(51) Int. Cl.
A61B 1/06 (2006.01)
A61B 19/00 (2006.01)
A61B 1/00 (2006.01)
A61B 1/04 (2006.01)
A61B 1/313 (2006.01)
A61B 5/00 (2006.01)
A61B 17/00 (2006.01)
A61B 17/32 (2006.01)
A61B 18/20 (2006.01)

(52) U.S. Cl.
CPC ............ *A61B 19/22* (2013.01); *A61B 1/00149* (2013.01); *A61B 1/00183* (2013.01); *A61B 1/041* (2013.01); *A61B 1/313* (2013.01); *A61B 1/3137* (2013.01); *A61B 5/6882* (2013.01); *A61B 17/00234* (2013.01); *A61B 34/32* (2016.02); *A61B 1/00193* (2013.01); *A61B 17/320068* (2013.01); *A61B 18/20* (2013.01); *A61B 2017/00221* (2013.01); *A61B 2017/00398* (2013.01); *A61B 2017/00734* (2013.01); *A61B 2034/742* (2016.02)

(58) Field of Classification Search
USPC .......... 600/106–107, 109, 114–115, 160, 173
See application file for complete search history.

(56) References Cited

U.S. PATENT DOCUMENTS 5,018,509 A * 5/1991 Suzuki et al. ................. 600/115
5,347,987 A * 9/1994 Feldstein et al. ............. 600/109
(Continued)

*Primary Examiner* — Matthew J Kasztejna
(74) *Attorney, Agent, or Firm* — Kenyon & Kenyon LLP

(57) ABSTRACT

The present invention provides a system and single or multi-functional element device that can be inserted and temporarily placed or implanted into a structure having a lumen or hollow space, such as a subject's abdominal cavity to provide therewith access to the site of interest in connection with minimally invasive surgical procedures. The insertable device may be configured such that the functional elements have various degrees of freedom of movement with respect to orienting the functional elements or elements to provide access to the site from multiple and different orientations/perspectives as the procedure dictates, e.g., to provide multiple selectable views of the site, and may provide a stereoscopic view of the site of interest.

20 Claims, 8 Drawing Sheets

Related U.S. Application Data

US2008/012347 on Oct. 31, 2008, now Pat. No. 8,810,638, application No. 14/073,483, which is a continuation-in-part of application No. PCT/US2012/047320, filed on Jul. 19, 2012.

(60) Provisional application No. 61/001,531, filed on Nov. 2, 2007, provisional application No. 61/054,282, filed on May 19, 2008, provisional application No. 61/510,797, filed on Jul. 22, 2011.

(56) References Cited

U.S. PATENT DOCUMENTS

| | | | |
|---|---|---|---|
| 5,836,869 A * | 11/1998 | Kudo et al. | 600/173 |
| 6,240,312 B1 * | 5/2001 | Alfano et al. | 600/476 |
| 8,512,229 B2 * | 8/2013 | Saadat et al. | 600/129 |
| 2004/0138529 A1 * | 7/2004 | Wiltshire et al. | 600/144 |
| 2005/0096502 A1 * | 5/2005 | Khalili | 600/106 |
| 2006/0189845 A1 * | 8/2006 | Maahs et al. | 600/146 |

* cited by examiner

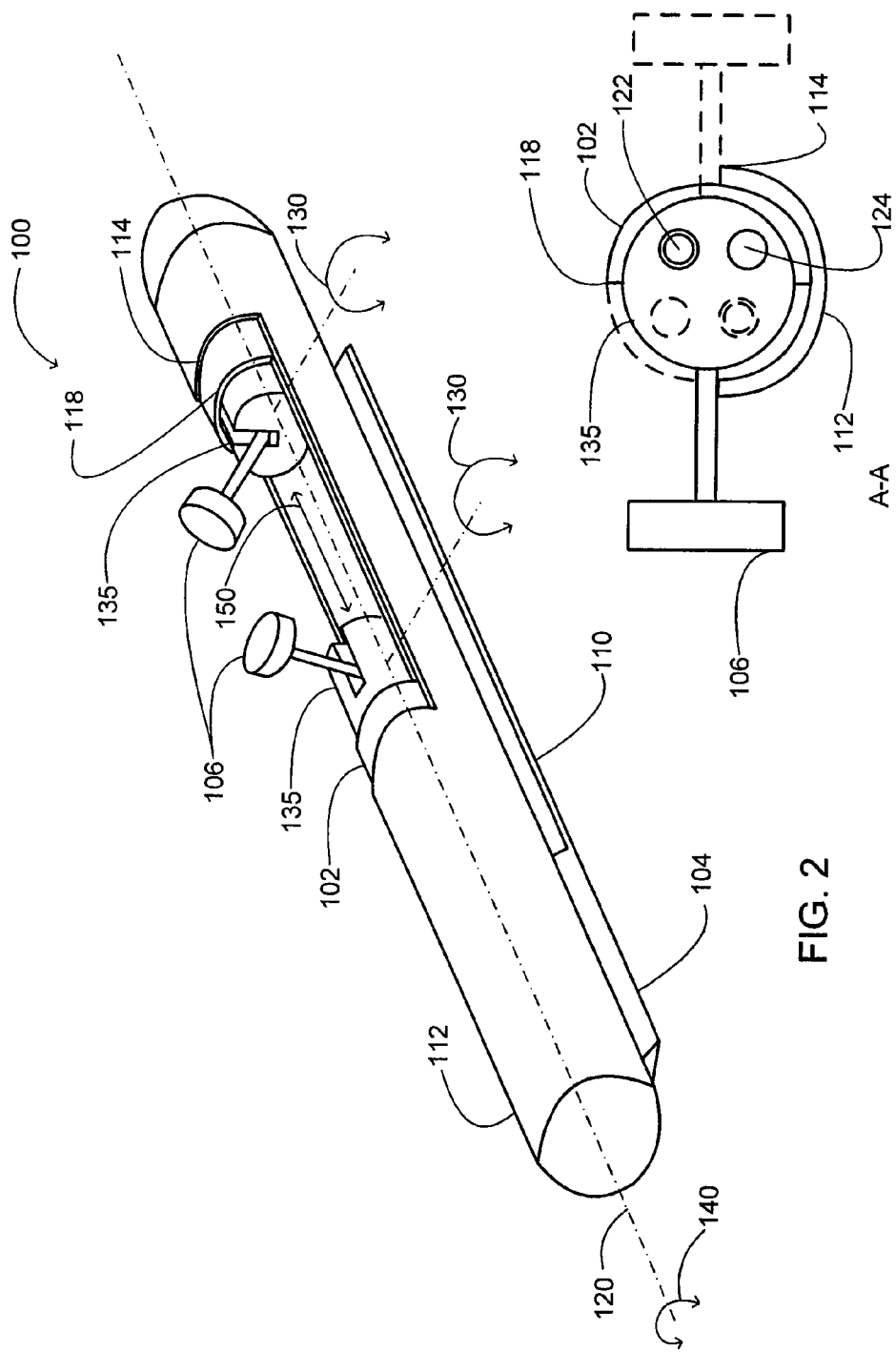

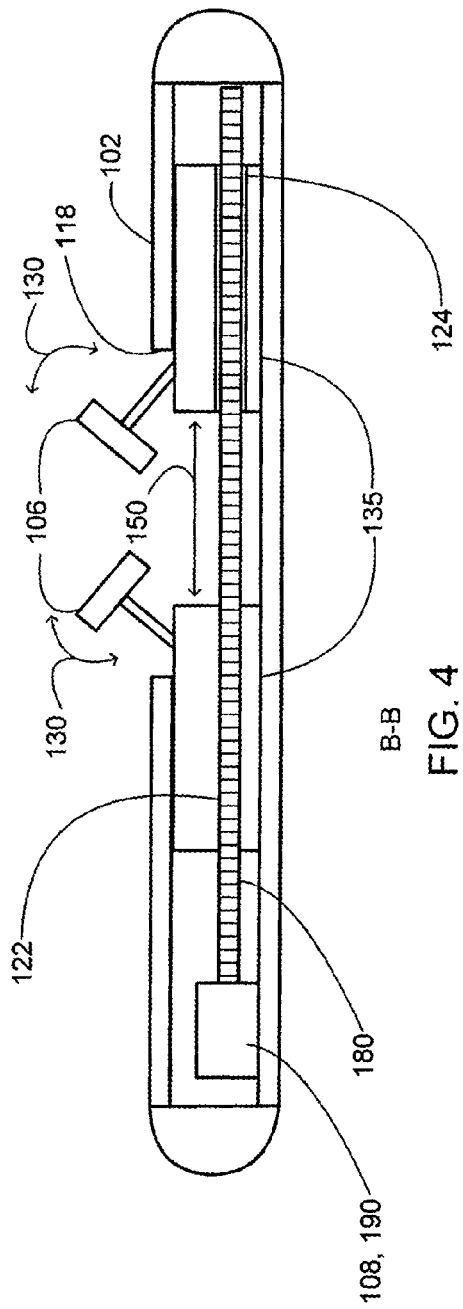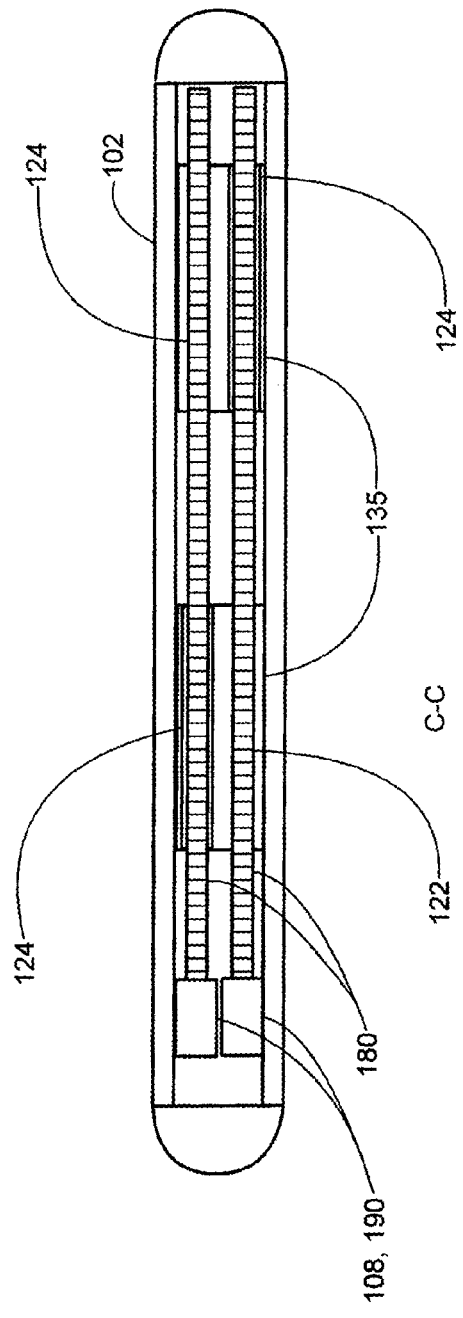

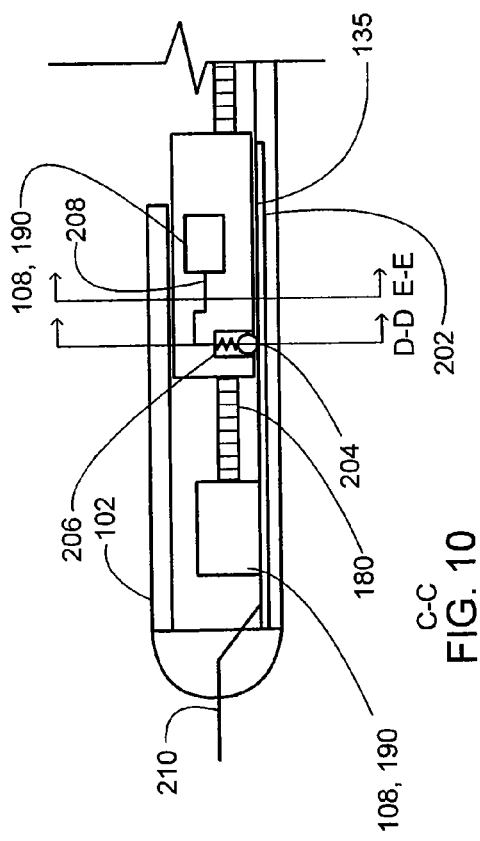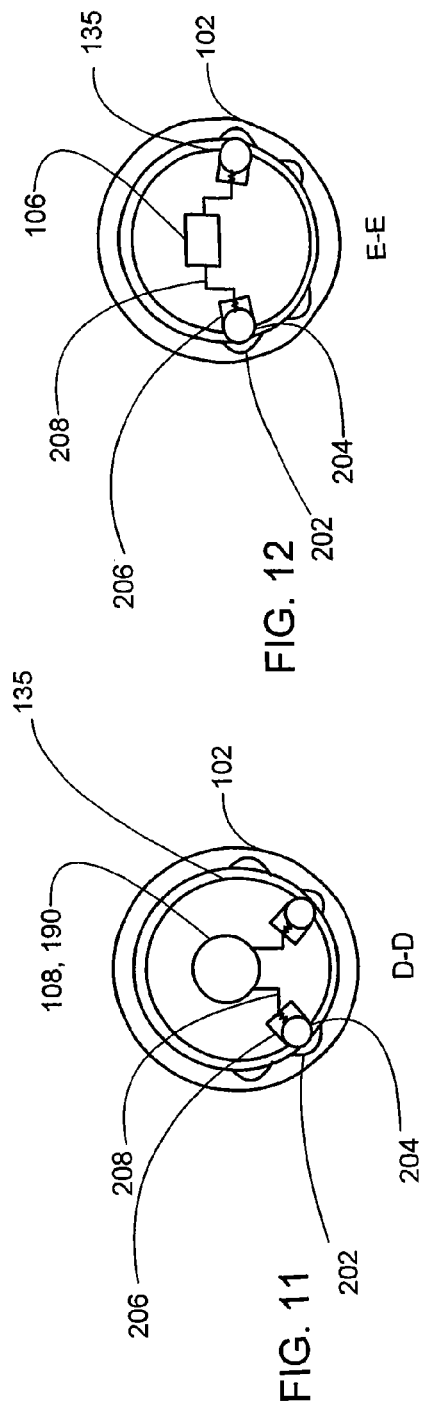

INSERTABLE DEVICE AND SYSTEM FOR MINIMAL ACCESS PROCEDURE

CROSS-REFERENCE TO RELATED APPLICATIONS

The present application is a divisional of U.S. patent application Ser. No. 11/475,737, filed on Jun. 26, 2006, which is a continuation of U.S. patent application Ser. No. 11/226,665, filed on Sep. 13, 2005, now abandoned, which is a continuation-in-part of U.S. patent application Ser. No. 10/620,298 filed on Jul. 15, 2003, now U.S. Pat. No. 7,066,879, each of which is expressly incorporated herein in its entirety by reference thereto. The present application is a continuation of U.S. patent application Ser. No. 12/066,559, which is the national stage entry of International Patent Application No. PCT/US2006/035858, filed on Sep. 13, 2006, which is a continuation of U.S. patent application Ser. No. 11/226,665, filed on Sep. 13, 2005, now abandoned, which is a continuation-in-part of U.S. patent application Ser. No. 10/620,298, filed on Jul. 15, 2003, now U.S. Pat. No. 7,066,879, each of which is expressly incorporated herein in its entirety by reference thereto. The present application is a continuation of U.S. patent application Ser. No. 12/770,246, filed on Apr. 29, 2010, which is a continuation-in-part of International Patent Application No. PCT/US2008/012347, filed on Oct. 31, 2008, which claims priority to U.S. Provisional Application Ser. No. 61/001,531, filed on Nov. 2, 2007, and U.S. Provisional Application Ser. No. 61/054,282, filed on May 19, 2008, each of which is expressly incorporated herein in its entirety by reference thereto. The present application is a continuation of International Patent Application No. PCT/US2012/047320, filed on Jul. 19, 2012, which claims priority to U.S. Provisional Application Ser. No. 61/510,797, filed on Jul. 22, 2011, each of which is expressly incorporated herein in its entirety by reference thereto.

BACKGROUND OF THE INVENTION

The present invention relates to systems and devices for use in connection with minimal or limited access procedures, such as minimally invasive surgical procedures.

Minimally invasive surgical procedures, e.g., laparascopic procedures, have dramatically reduced patient recovery times. However, the reduced recovery times have correspondingly resulted in an increase, from a surgeon's perspective, in the complexity of the surgical procedures. This is in part due to the characteristic relatively small incisions, e.g., approximately 10 mm in diameter, through which a surgeon accesses a surgical site to perform the minimally invasive surgery. The limited access adds to the complexity of the surgical procedures since surgeons must remotely manipulate sufficiently small instruments though the incisions and must also view the surgical site through the small incisions.

Imaging systems that provide a view of the surgical site for a minimal access surgical procedure typically include an endoscope, e.g., a tubular instrument containing optical lenses and light guides that feed images to an external video camera and a monitor, such as the endoscope discussed in U.S. Pat. No. 4,651,201. Endoscopes, however, have drawbacks. For instance, since the surgeon is generally using both hands to manipulate other instruments used in the procedure, e.g., forceps, scissors, coagulators/cauterizer probes, etc., an assistant is required to hold and orient the endoscope to adjust the view during the procedure. Robotics have recently been introduced to automate the task of orienting the endoscope during minimally invasive surgical procedures, such as the Automated Endoscopic System for Optimal Positioning ("AESOP"). The AESOP uses a robot arm that is directed by spoken commands to orient the endoscope. While the AESOP takes the burden off the assistant and provides a much more stable view of the field, the equipment necessary for the AESOP is complex and occupies a large part of the operating room floor.

A smaller and simpler robotic endoscope manipulator that can be placed directly over the insertion point was developed at the Institut National de Recherche en Informatique et en Automatiqueinria ("INRIA"). However, the INRIA system as well as other robotic systems fail to address the limited available range of motion about the fulcrum at the abdominal wall through which the endoscope as well as other instruments pass to gain access to the surgical site. The limited range of motion translates into limits with regard to the degree of freedom that the instruments may be oriented toward the surgical site.

Active or hyper endoscope systems have been proposed that generally consist of a multi-link robotic arm with a camera mounted thereon, such as the active endoscope discussed in Japanese Patent 2000175865, which is hereby incorporated herein by reference, which provide additional freedom with respect to orienting the endoscope camera. However, these systems require a dedicated incision for the endoscope to access the surgical site and typically require relatively high voltage to operate the actuators necessary to manipulate the hyper endoscope which from a safety perspective may be problematic when used in surgical procedures. Pill cameras have also been adapted for imaging sections of the small intestine that are out of the reach of a colonoscope, such as the pill camera described in U.S. Pat. Nos. 5,604,531 and 6,428,469. However, pill cameras do not generally include means for orienting the camera; rather, pill cameras merely rely on peristalsis to orient the camera.

There is therefore a need for systems and devices for minimal access procedures that do not require an assistant to hold and orient an instrument and that provide additional or greater freedom than is provided with an endoscope or other instrument with regard to orienting the instrument toward the site of interest. There is also a need for systems and devices for minimal access procedures that provide additional or greater freedom with regard to orienting the instrument toward a site of interest than is provided with an active or hyper endoscope that do not require a dedicated access incision into the site for the instrument.

SUMMARY OF THE INVENTION

The present invention generally provides a single or multifunctional element insertable device that can be inserted and temporarily placed or implanted into a structure having a lumen or hollow space. Once inserted into the lumen of the structure, the device is removably attached or secured to the interior of the structure, such as to the interior of a subject's abdominal wall, near a site of interest so that the functional element or elements may be oriented thereto, preferably to look down at the area of interest. The insertable and implantable aspect of the present invention obviates the limited motion about an insertion point drawback associated with endoscopes, as well as other instruments, by allowing the surgeon to move the device to different locations on the abdominal wall. Moreover, the insertable aspect allows a surgeon to insert a plurality of devices into the structure's lumen through a single incision thereby increasing access to the site with minimal incisions. Although the present invention may be described by way of example in relation to minimal invasive surgical procedures, it is understood that the invention is equally applicable to provide images, as well as various other functionality, of numerous structures with a lumen, and is therefore not limited thereto. Imaging is used herein to generally denote pertaining to producing an image of a site, such as producing a video image of a surgical site.

The present invention further provides an insertable device that has one or more functional elements configured to have or exhibit various degrees of freedom of movement with respect to orienting the functional elements. Where the functional element or element is a camera element, the device provides a wider field of view of the surgical site than that provided by standard endoscopic cameras. Additionally, the insertable device so configured provides access to a site of interest from multiple and different orientations or perspectives within the lumen, as the procedure dictates, further obviating limited mobility about the point of insertion drawback associated with endoscopes. In a multi-camera element embodiment of the invention, the imaging device provides multiple selectable views of the site and may be used in connection with a stereoscopic imaging system to provide a stereo view of the surgical site to recreate the sense of depth that is lost with a traditional video monitor.

Accordingly, in one aspect of the present invention, a device insertable into a structure having a lumen is provided that includes a first housing, at least one functional element connected to the first housing, the functional element for use during a minimal access procedure, and a securing element for removably securing the insertable device to or against a wall of a structure having a lumen. In one embodiment, the at least one functional element is movably connected to the first housing, and the device includes at least one actuating element connected to the first housing and the functional element. The actuating element is generally capable of moving the functional element in relation to the first housing in at least one degree of freedom. The securing element may be a needle protruding from the imaging device essentially inline with the elongated axis of the device, a magnet, a clamp, an adhesive, etc. In one embodiment, the insertable device is adapted or otherwise configured for use in connection with minimal access surgical procedures. In this instance, the securing element includes a needle protruding from the insertable device essentially inline with the elongated axis of the device. The insertable device is capable therewith of being removably secured against a subject's abdominal wall by inserting the needle into tissue of the abdominal wall.

The functional elements may vary according to the desired functionality, which includes camera elements, a light elements, a laser elements, etc. In one embodiment, the functional element includes a camera element, such as a CMOS imaging sensor or a CCD image sensor. In another embodiment, the functional element is a camera element that includes a lens and a CCD image sensor mounted in a lens housing having threads therein to accept the lens and to accommodate focal adjustments.

In one embodiment, at least one functional element is movably connected to the first housing and the device includes at least one actuating element connected to the first housing and the functional element. In this instance, the actuating element is capable of moving the camera element in relation to the first housing in at least one degree of freedom selected from a group consisting of: a first degree of rotational freedom essentially orthogonal to the elongated axis; a second degree of rotational freedom essentially inline with the elongated axis; and a third degree of translation freedom essentially inline with the elongated axis.

In another embodiment, the at least one functional element is a plurality of camera elements movably connected to the first housing and the device includes a plurality of actuating element connected to the first housing and the camera elements. In this instance, the actuating elements are capable of moving each of the camera elements in relation to the first housing in at least one degree of freedom selected from the group noted above.

In another embodiment, the at least one functional element is movably connected to the first housing and the device includes at least one actuating element connected to the first housing and the functional element. In this instance, the actuating element is capable of moving the camera element in relation to the first housing in a first degree of rotational freedom essentially orthogonal to the elongated axis allowing the functional element to be retracted into and extracted from the first housing. The actuating elements may be a motor producing rotational movement that interfaces with the functional element to translate or redirect the rotational movement produced by the motor in a direction essentially orthogonal to the elongated axis, such as with a bevel screw, a worm gear, or an assembly linking the element to a nut on a lead screw.

In another embodiment, the insertable device includes a second housing rotatably attached to the first housing and at least one actuating element connected to the first and second housings. In this instance, the actuating element is capable of moving the functional element in relation to the first housing in a second degree of rotational freedom essentially inline to the elongated axis by rotating the first housing in relation to the second housing.

In another embodiment, the at least one functional element is movably connected to the first housing and the device includes at least one actuating element connected to the first housing and the functional element. In this instance, the actuating element is capable of moving the functional element in relation to the first housing in a third degree of longitudinal freedom essentially inline to the elongated axis allowing the functional element to translate along the third degree of freedom.

Movement in a third degree of longitudinal freedom may be accomplished with a functional element that is mounted to a shuttle capable of moving along the elongated axis. The actuating element may be a motor producing rotational movement connected to a lead screw that interfaces with a threaded portion of the shuttle to translate the rotational movement of the motor into longitudinal movement in the shuttle along the elongated axis. Such movement may also be accomplished for a plurality of functional elements with a corresponding number of motors producing rotational movement, and a corresponding number of shuttles each functional element is mounted to a shuttle capable of moving along the elongated axis. In this instance, each shuttle includes a threaded portion and a hole, and each motor connected to a lead screw interfaces with the threaded portion of one of the shuttles to translate the rotational movement of the motor into longitudinal movement in the shuttle along the elongated axis and each lead screw passes through the hole of another shuttle to provide a guide for the other shuttle. Each shuttle may include mounted thereto at least one actuating element capable of moving the functional elements in relation to the first housing in a first degree of rotational freedom essentially orthogonal to the elongated axis allowing the functional elements to be retracted into and extracted from the first housing. In one embodiment, the plurality of actuating elements are capable of moving each of the functional elements independently of each other. The translational movement may also be accomplished with a linear rail/actuator system.

In another embodiment, the insertable device includes a second housing rotatably attached to the first housing and at least one actuating element connected to the first and second housings. In this instance, the actuating element is capable of rotating the first housing in relation to the second housing and each housing has an access opening therein capable of aligning with each other so that the first housing may be rotated to cover the functional elements and rotated to align the access openings to expose the functional element.

In another aspect of the present invention, an insertable device having an elongated axis associated therewith is provided that includes a first housing, a second housing rotatably connected to the first housing, at least one camera element comprising an image sensor movably connected to the first housing, at least one actuating element connected to the first housing and the camera element, and a securing element associated with the second housing for removably securing the imaging device to or against a wall of a structure having a lumen. The actuating element is capable of moving the camera element in relation to the first housing in at least one degree of freedom selected from a group consisting of: a first degree of rotational freedom essentially orthogonal to the elongated axis, a second degree of rotational freedom essentially inline with the elongated axis, and a third degree of longitudinal freedom essentially inline with the elongated axis.

In another aspect of the invention, an insertable device having an elongated axis is provided that includes a first housing, a second housing rotatably connected to the first housing, a plurality of camera elements each comprising an image sensor movably connected to the first housing, at least one actuating element connected to the first housing and the second housing, the actuating element capable of rotating the first housing in relation to the second housing, at least one actuating element connected to each of the camera elements, the actuating element capable of moving the camera element in relation to the first housing in a first degree of rotational freedom essentially orthogonal to the elongated axis, and a securing element associated with the second housing for removably securing the imaging device to or against a wall of a structure with a lumen.

In another aspect of the invention, a minimal access system is provided that includes a driving device communicatively connected to at least one device insertable into a structure having a lumen, the device including at least one functional element associated therewith for use during a minimal access procedure and at least one securing element for securing the insertable device against a wall of the structure having a lumen. In one embodiment, the insertable device includes at least one actuating element capable of moving the functional element in at least one degree of freedom and the driving device provides a drive signal to remotely control the movement of the functional element.

The driving device may be adapted to provide hybrid control of the insertable device such that the driving device may autonomously control functional element movement in at least one degree of freedom. For instance, the functional element may be a camera element and the driving device may autonomously control the camera element movement to maintain a user identified object in view while the user controls camera element movement in at least one degree of freedom to obtain an image of the site of interest from different perspectives. Additionally, the at least one functional element may be a plurality of camera elements and the driving device may autonomously control the movement of the camera elements to produce a stereoscopic image of the site of interest or to create stereo images of a site of interest in real-time based on automatic vergence algorithms.

In another aspect of the invention, an insertable device is provided that includes a first housing, at least one functional element movably connected to the first housing allowing the functional element to be retracted into and extracted from the first housing, and at least one actuating element connected to the first housing and the functional element. The actuating element is generally capable of moving the functional element in relation to the first housing in a first degree of rotational freedom essentially orthogonal to an elongated axis of the device for retracting and extracting the functional element from the first housing.

In another aspect of the invention, an insertable device is provided that includes a first housing, a second housing rotatably connected to the first housing, at least one camera element that includes an image sensor movably connected to the first housing, and at least one actuating element connected to the first housing and the camera element. The actuating element is generally capable of moving the camera element in relation to the first housing in at least one degree of freedom, such as a first degree of rotational freedom essentially orthogonal to an elongated axis of the device, a second degree of rotational freedom essentially inline with the elongated axis, and a third degree of longitudinal freedom essentially inline with the elongated axis.

In another aspect of the invention, a minimal access system is provided that includes a driving device communicatively connected to at least one device insertable into a structure having a lumen. The insertable device includes a first housing, at least one functional element for use during a minimal access procedure movably connected to the first housing allowing the functional element to move in at least one degree of freedom, and at least one actuating element connected to the first housing and the functional element. The actuating element is generally capable of moving the functional element in relation to the first housing in the at least one degree of freedom. The driving device includes at least one controller that provides a driving signal to control movement of the functional element in the at least one degree of freedom.

In another aspect of the invention, a minimal access system is provided that includes a driving device communicatively connected to at least one device insertable into a structure having a lumen. The insertable device includes a first housing, at least one camera element moveably connected to the first housing allowing the camera element to move in at least one degree of freedom, and at least one actuating element connected to the first housing and the camera element. The actuating element is generally capable of moving the camera element in relation to the first housing in the at least one degree of freedom. The driving device includes at least one controller that provides a driving signal to control movement of the camera element in the at least one degree of freedom, and an image tracking module that tracks movement of at least one object in a field of view of the camera element. In this instance, the controller controls movement of the camera element based on a signal from the image tracking module to maintain the object in the field of view of the camera element.

Additional aspects of the present invention will be apparent in view of the description that follows.

BRIEF DESCRIPTION OF THE FIGURES

FIG. 2 is a perspective view of an insertable device for minimal access procedures according to one embodiment of the present invention with functional elements in an extracted position;

FIG. 3 is a sectional view of an insertable device for minimal access procedures according to one embodiment of the present invention showing a functional element in an extracted position and showing the range of motion of the functional element in a direction orthogonal to the elongated axis of the device;

FIG. 4 is a sectional view of an insertable device for minimal access procedures according to one embodiment of the present invention showing functional elements each rotatably mounted onto a shuttle and a shuttle interfacing with a motor and lead screw assembly;

FIG. 5 is a sectional view of an insertable device for minimal access procedures according to one embodiment of the present invention showing shuttles each interfacing with a motor and lead screw assembly;

FIG. 10 is a sectional view of an insertable device for minimal access procedures according to one embodiment of the present invention showing an electrical circuit for communicating with the functional element and/or the shuttle;

FIG. 11 is a sectional view of an insertable device for minimal access procedures according to one embodiment of the present invention showing an electrical system with a plurality of circuits for communicating with the functional element and/or the shuttle;

FIG. 12 is a sectional view of an insertable device for minimal access procedures according to one embodiment of the present invention showing an electrical system with a plurality of circuits for communicating with the functional element and/or the shuttle;

DETAILED DESCRIPTION OF THE INVENTION

In one aspect of the present invention, a single or multifunctional element, insertable device is provided that can be inserted and temporarily placed or implanted into a structure having a lumen or hollow space. The structure having a lumen may be the anatomical structure of a subject, such as the subject's heart, lungs, esophagus, stomach, intestines, thoracic cavity, abdominal cavity, blood vessels, etc., and non-anatomical structure, such as tanks, pipes, confined spaces, rooms, etc. In one embodiment, the present invention is adapted to be inserted and temporarily implanted into a subject's abdominal cavity to provide therewith images of a surgical site for use in connection with minimally invasive surgical procedures, such as laparascopic procedures. The subject may be any animal, including amphibians, birds, fish, mammals, and marsupials.

Figure 1:
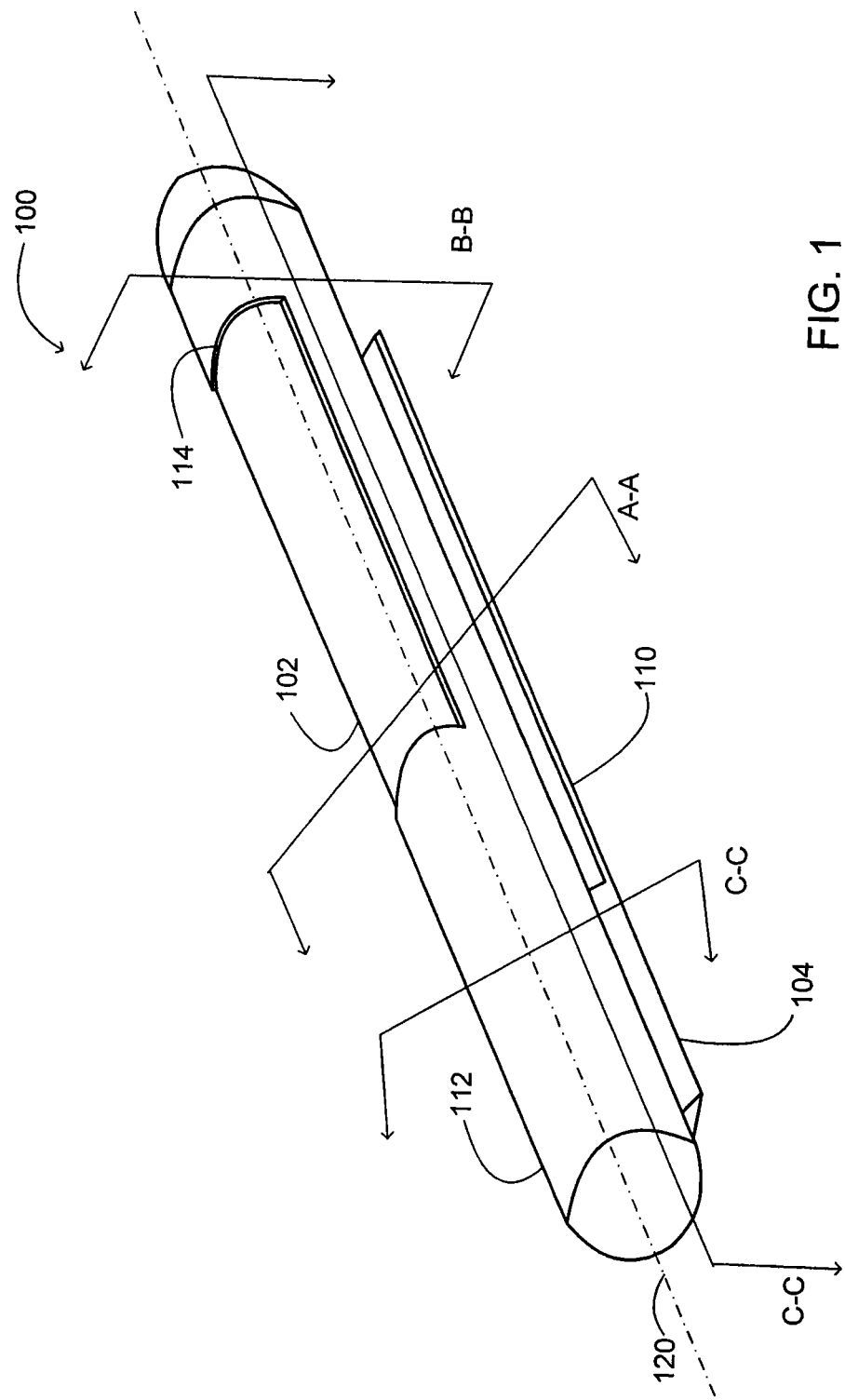
FIG. 1 is a perspective view of an insertable device for minimal access procedures according to one embodiment of the present invention functional elements in a retracted position.

Referring to FIGS. 1 and 2, the insertable device 100 of the present invention generally includes a first housing 102 and a securing element 104 for removably securing, e.g., attaching or holding, the device onto or against the wall of a structure having a lumen, at least one functional element 106 movably attached to the housing, and at least one actuating element 108 connected to the first housing for moving or causing the functional element to move in relation to the housing. A functional element is generally an instrument or device that provides a desired functionality with regard to the minimal access procedure. For instance, the functional element 106 may be a data acquisition device, such as a camera element, a sensor, an ultrasound probe, etc., or an effector, such as a light element, a laser element, a grasper, a dissecting instrument, a needle, a scalpel, a grasper, dithermy/cautery instruments, a suturing instrument, a stapling instrument, etc. An effector is generally a device or a combination of devices that bring about a result. The device 100 may further include a second housing 112 movably connected to the first housing 102, which is explained in more detail below.

In one embodiment, the insertable device is adapted or otherwise configured for surgical applications. In this instance, the securing element 104 may be a needle 110 protruding from the insertable device 100, e.g., the first or second elongated housings 102, 112, in an orientation essentially parallel to or inline with the elongated axis 120, similar to the pocket clip of a pen, such that the needle 110 may be inserted into the inner fatty tissue beneath the muscle layer of the abdominal wall to secure the device 100 to the abdominal wall. It is understood that dimensions of the needle may vary, however, the dimensions may be limited in order to limit the size of the penetration or incision created by the needle as it is inserted into the tissue and correspondingly to allow the penetration or incision to heal relatively quickly after the operation. In one embodiment, the needle 110 has a rectangular cross section and is limited to dimensions of about 1 mm by about 3 mm. The securing element 104 may alternatively be a magnet or a material attracted to a magnet, which may be used to removably secure the insertable device to the abdominal wall with corresponding magnets placed outside the body to hold the device against the abdominal wall, a clamp, an adhesive substance, a tab or hole that facilitates, e.g., suturing or stapling the device 100 to the abdominal wall, etc. The type and configuration of the securing element 104 may vary depending further on the particular application for which the device is adapted.

Where the functional element 106 is a camera element, the type of camera system adapted for the insertable device 100 may vary as well, however, to facilitate use of the device for minimal access procedures, e.g., minimal access imaging, the camera system selected for the device 100 must accommodate the compact dimensions of the device 100 as dictated by the dimensions of the opening though which access into the structure with a lumen is provided. Where the device 100 is adapted for use in connection with minimally invasive surgical procedures, for instance, the dimensions of the device 100 will generally be dictated by the size of the port or trocar that provides access to the site, e.g., a port about 20 mm in diameter. A compact size with respect to the camera portion of the device 100 may be achieved, for example, with CMOS or CCD sensor chip based cameras that consist of relatively compact elements that may be located remote from each other. In one embodiment, the camera is a chip based camera with remote camera elements, such as a remote CCD image or CMOS image sensor assemblies, which allow the image sensing portion of the camera that is introduced into the surgical site to be movable in relation to the rest of camera circuitry. In another embodiment, the camera includes a 8 mm round CCD color image sensor mounted essentially perpendicular to a 17 mm long driver board, and the driver board is electrically connected to a camera control unit ("CCU") remote from the insertable device 100.

Various types and numbers of actuating elements 108 or actuators for moving the functional element in relation to the housing may be used to achieve the desired degree of freedom with regard to the movement of the functional element 106, such as piezoelectric actuators, pneumatic actuators, solenoids, shape memory alloy actuators, linear motors, motors producing rotational movement, motors producing rotational movement adapted to provide linear movement, etc. The type of actuating element 108 and the number of actuating elements 108 will vary depending on the design constraints of the insertable device 100, e.g., the dimensions as dictated by the size of the access port or opening, the degrees of freedom the functional element or elements 106 are intended to move, the number of functional element, etc. In one embodiment, at least one of the actuating elements 108 comprises a brushless DC motor producing sufficient torque to produce the desired movement in the functional element 106. The DC motor may further be connected to a lead screw which when rotated can translate a shuttle or carriage 135 in both directions along the axis of the lead screw to produce linear motion and with a bevel screw or worm gear assembly to redirect the rotational movement produced by the motor. In one embodiment, the motor runs on 6 volts, is about 27 mm long, and has a diameter of about 5 mm.

Figure 8:
FIG. 8 is a side view of an insertable device for minimal access procedures according to one embodiment of the present invention with functional elements in a retracted position.
Figure 9:
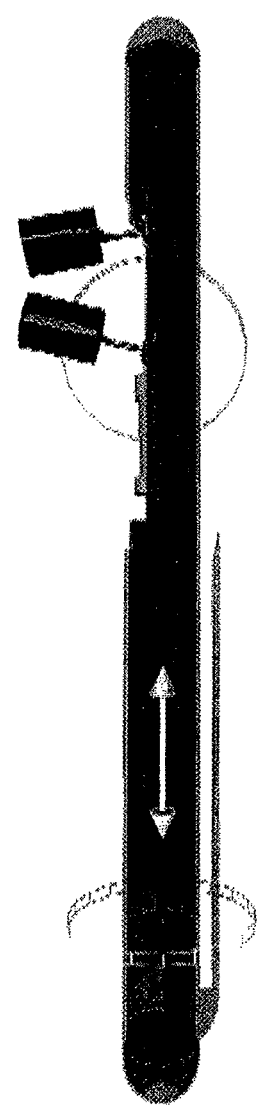
FIG. 9 is a side view of an insertable device for minimal access procedures according to one embodiment of the present invention with functional elements in an extracted position.

In at least one embodiment, the device 100 is designed to provide various degrees of freedom with regard to the movement of the one or more functional elements 106. The degrees of freedom will generally be described herein in relation to the elongated axis 120 of the device 100. The various degrees of freedom may also be described in relation to the image plane, where, for instance, panning may be viewed as a rotation, generally about a vertical axis through the image plane, tilting about a horizontal axis through the image plane, and rolling would be about the optical axis. For instance, a first degree of rotational freedom 130 essentially orthogonal to the elongated axis 120 of the device 100 which allows the element or elements 106 to be retracted into and extracted from the housing 102 and also allows the element or elements 106, e.g., the camera or cameras, to pan along the first degree of freedom 130, as shown between FIG. 8 and FIG. 9. A second degree of rotational freedom 140 essentially parallel or inline with the elongated axis 120 allows the element or elements 106 to tilt along the second degree of freedom 140. A third degree of longitudinal freedom 150 essentially parallel or inline with the elongated axis 120 allows the element or elements 106 to translate along the third degree of freedom 150. In the case of a multiple functional element device, the multiple elements 106 may be independently or simultaneously rotated and/or moved in the first and third degrees of freedom 130, 150, and in tandem in a second degree of freedom 140. This particular feature is suited, for instance, where the multiple elements 106 are camera elements for use in stereoscopic imaging. In other instances, the multiple functional elements 106 may be independent from each other and thus may be independently or stimulatingly rotated and/or moved in a first, second, and third degrees of freedom, 130, 140, 150.

The various degrees of freedom provide access to or views of the site of interest from multiple and different orientations/viewpoints. Additionally, the various degrees of freedom of movement in addition to independent control may, in a stereoscopic imaging system, provide flexibility with regard to controlling the vergence angle of the stereo pair of camera elements and establishing a baseline for stereo imaging, and, in an autonomous tracking system, maintaining moving objects in the field of view. In one embodiment, the insertable device 100 includes five actuating elements 108, e.g., motors, which control the movement of two functional elements 106 that may be moved in the first, second, and third degrees of freedom 130, 140, 150. In one embodiment, the functional elements 106 are camera elements and the zoom and certain rotations may be accomplished in software with imaging processing capability.

Since the insertable device 100 is intended to provide functionality with respect to minimal or limited access procedures, it may be desirable to limit at least one of the overall dimensions of the device 100 to facilitate insertion into the structure with the lumen through a relatively small access opening. For example, for minimally invasive surgical procedures, an elongated tubular and/or cylindrical insertable device 100 may be configured to allow for insertion through an access port having a diameter of up to about 20 mm. Accordingly, in one embodiment, the insertable device 100 is configured to have a diameter of about 20 mm or less.

To achieve the various degrees of freedom the actuating elements 108 must generally be configured so that the actuating elements 108 fit within the dimensions of the device 100. If motors producing rotational movement, for instance, are used to provide the motive force for the functional elements 106, at least with respect to a device 100 having a diameter of about 20 mm or less, the motor will likely need to be aligned lengthwise essentially inline or parallel to the elongated axis 120 since motors typically exceed the 20 mm or less dimensional constraints of the device 100. Accordingly, motors may beneficially be used to provide rotational movement along the second degree of freedom 140, may be combined with a lead screw and shuttle arrangement to provide longitudinal movement along the third degree of freedom 150, and may be combined with a worm gear or bevel screw arrangement to provide rotational movement along the first degree of freedom 130.

In one embodiment the device 100 includes a second elongated housing 112 that is rotatably connected to the first elongated housing 102, with or without bearings, such that the first and second housings 102, 112 may be rotated in relation to each other in at least one degree of freedom. In this instance, the device 100 may be removably secured to the wall of the structure having a lumen, e.g., the abdominal wall, with the securing element that is an aspect of the second housing 112. In this instance, tilting along the second degree of freedom 140 may be achieved by rotating the first housing 102, which includes the functional element or elements 106 therein, in relation to the second housing 112. The first and second housings 102, 112 may be rotated with respect to each other with a motor that produces rotational movement appropriately connected to each of the housings 102, 112.

It is understood that the second housing 112 may occupy various portions of the length of the device 100. For instance, the second housing 112 may be long enough in relation to the elongated axis 120 to provide a sufficient bearing surface to withstand bending forces applied to the device 100 without occupying the full length of the device 100. The greatest amount of rotational freedom in the direction of the second degree of freedom 140 may be achieved in this instance if the second housing 112 does not interfere with the movement of the functional elements 106 while the elements 106 are in an extracted position. The second housing 112 may occupy a greater portion of the length of the device 100 to provide a protective cover for the functional elements 106. In this instance, the second housing 112 will include an access opening 114 capable of aligning with an access opening 118 of the first housing 102 so that second housing 112 will cover functional elements 106 retracted within the first housing 102 for insertion into the structure and, once inserted or removably secured to the structure, the first housing 102 may be rotated, e.g., 180 degrees, to reveal the functional elements 106 though the access openings 114. The access opening 118 of the first housing 102 may further allow the functional element or elements 106 to retract into and extract from the first housing 102. In one embodiment, the access openings 114, 118 of the first and second housings 102, 112 are sized to allow the maximum amount of rotational movement along the second degree of freedom 140, e.g., the access opening 114 of the second housing 112 is dimensionally equal to or greater circumferentially than the access opening 118 of the first housing 102, as shown in FIG. 3. In one embodiment, the first and second housing are capable of being rotated at least 270 degrees with respect to each other when the functional elements 106 are in a retracted position and/or at least 180 degrees with the functional elements 106 extracted.

In one embodiment, the longitudinal movement in the direction of the third degree of freedom 150 is produced by mounting at least one functional element 106 onto a shuttle 135 that is capable of moving along the elongated axis 120 within the lumen of the first housing 102. Each shuttle 135 further includes an actuating element 108 associated therewith for producing the longitudinal movement within the first housing 102. Referring to FIGS. 4 and 5, in one embodiment, the shuttle 135 is moved along the elongated axis 120 within the first housing 102 by a motor 190 connected to a lead screw 180 that interfaces with a threaded portion 122 of the shuttle 135. Accordingly, the shuttle 135 moves within the first housing 102 as the lead screw 180 is screwed and unscrewed in relation to the shuttle 135. A track or guide may be provided within the first housing 102 and a corresponding key in the shuttle 135 to restrict undesirable rotation of the shuttle 135. A second shuttle 135 with a threaded portion 122 having threads in a reverse direction than that the first shuttle 135 may interface with the lead screw 180 with corresponding reverse threads to move the shuttles 135 within the first housing 102 in directions to and from each other. In one embodiment, independent longitudinal movement for each of the shuttles 135 is achieved with a motor 190 and lead screw 180 combination for each of the shuttles 135. Rotational movement for each shuttle 135 may be restricted with a guide and key arrangement as noted above, or, alternatively, with each other's lead screw. In this instance, each shuttle 135 includes a threaded portion 122 that interfaces with one lead screw 180 connected to a respective motor 190 associated with the shuttle and one hole 124 larger than the threads of the lead screw 180 connected to the motor 190 associated with the other shuttle 135 which allows the shuttles to use each other's lead screw 180 as a guide.

Figure 6:
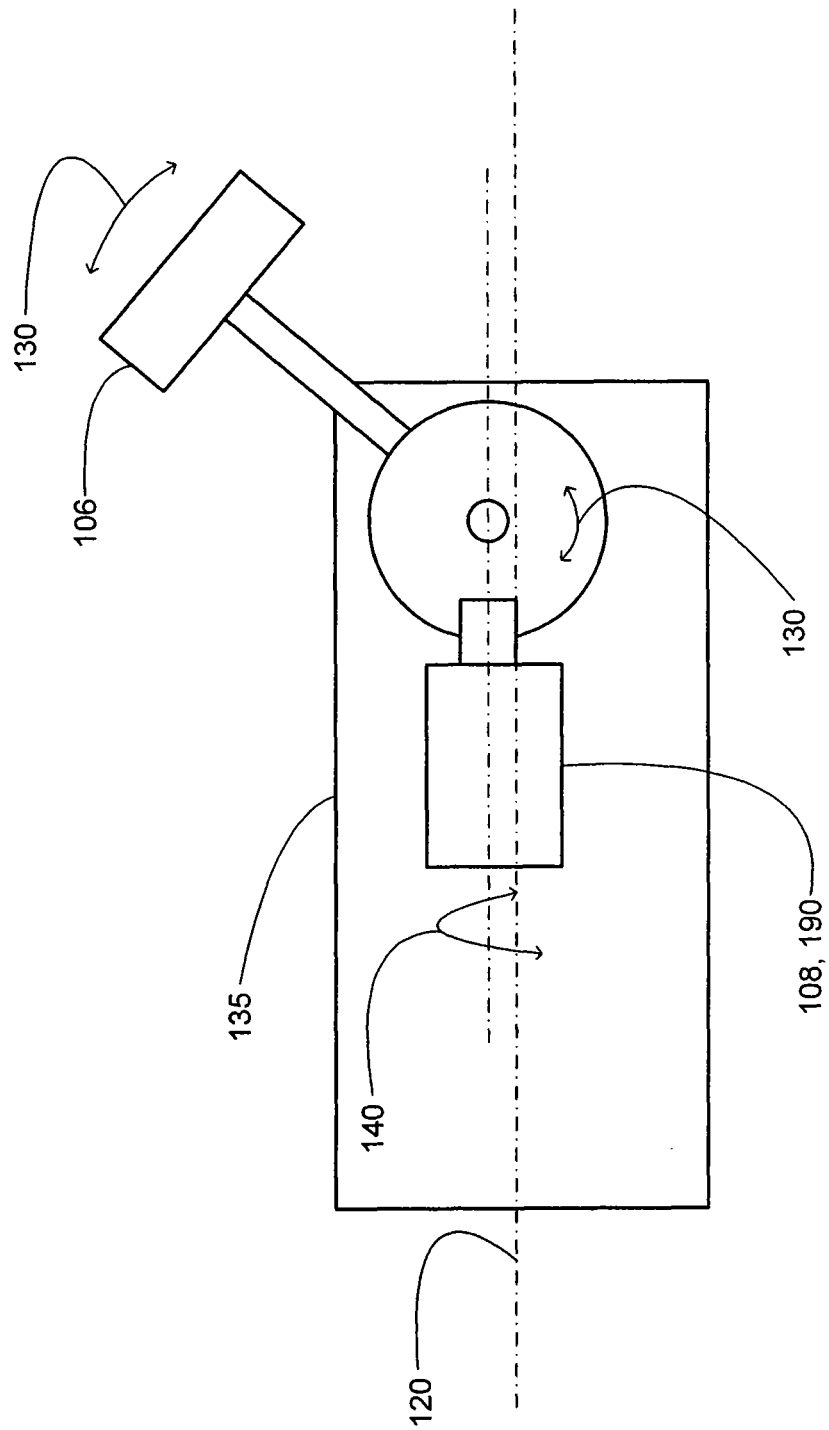
FIG. 6 is a perspective view of a shuttle with a functional element rotatably mounted thereon and the functional element interfacing with a motor with a worm gear assembly.

Rotational movement in the direction of the first degree of freedom 130 is achieved with an actuation element 108 that engages the functional element 106 to retract and extract the functional elements into and out of the device 100. In one embodiment, the actuation element 108 is a motor 190 that interfaces with functional element 106 with a worm gear assembly to redirect the rotation produced by the motor 190 in a direction essentially orthogonal or essentially perpendicular to the axis of the motor 190 or the elongated axis 120, as shown in FIG. 6. In one embodiment, the functional elements 106 are mounted to the shuttles 135 so that maximum freedom in the direction of the third degree of freedom 150 is achieved, e.g., in a manner such that the functional elements appear to face each other. In one embodiment, the distance between the functional elements 106 or shuttles is up to 10 mm.

In one embodiment, at least one of the functional elements 106 is a camera element and the shuttle 135 includes a camera element rotatably attached thereto which includes an image sensor, such as a CCD or CMOS image sensor, mounted in a lens housing that has threads therein to accept a lens with matching threads which accommodates focal adjustments. In one embodiment, a CCD sensor and lens are mounted on a pedestal, which is rotatably connected to the shuttle 135 so that the pedestal may tilt about an axis that is orthogonal to the shuttle motor. The driver board mounted on the shuttle 135 may be connected to the CCD image sensor with or without a flexible ribbon cable.

It is understood that the various components of the device 100 may be manufactured from a variety and/or a combination of biocompatible and non-biocompatible materials, such as polyester, Gortex, polytetrafluoroethyline (PTFE), polyethelene, polypropylene, polyurethane, silicon, steel, stainless steel, titanium, Nitinol, or other shape memory alloys, copper, silver, gold, platinum, Kevlar fiber, carbon fiber, etc. Where non-biocompatible materials may come into contact with anatomic structure, the components made from the non-biocompatible materials may be covered or coated with a biocompatible material. In one embodiment, the housings 102, 112 of the device 100 are manufactured from stainless steel. The housings may be stainless steel tubes of various diameters. In one embodiment, the second housing 112 has a diameter of about 5 mm (0.197") to about 25 mm (0.984"), and is about 127 mm (5") to about 228 mm (9") long. In one embodiment the second housing has a diameter or of 9/16" and is about 7.8" long. In another embodiment, the device has a wall thickness of 0.028". The device may further have spherical end caps to ease insertion into the structure. An about 50 mm (2") to about 152 mm (6") long section of the second housing 112 may be cut away to produce an access opening 114 which allows the functional elements 106 to tilt when extracted. In on embodiment, the access opening is about 2.6" long. In one embodiment, the first housing 102 has a 0.028" thickness. In another embodiment, the first housing has a smaller diameter than the second housing which is also between about 5 mm to 25 mm and a length of about 127 mm to about 228 mm. In one embodiment, the first housing has a ½" diameter and is 6" long. A portion of the first housing 102 is cut away to produce an access opening 118 to allow the cameras to be retracted therein and extracted therefrom. The first housing 102 preferably includes sufficient space to house cable to provide sufficient slack to accommodate the movement of the functional elements 106 as described herein.

It is understood that the device 100 may be adapted to provide additional functionality. For instance, the functional element 106 may be an effector type instrument, such as a light for illuminating the site of interest, a laser for cauterizing, coagulating, or ablation, a scissors, ultrasonic dissector or other types of dissecting instrument, a needle, a grasper, a scalpel, diathermy/cautery instruments, a suturing instrument, a stapling instrument, or any other type of surgical instrument. The instrument may be fixed in relation to the device or may be moveable in relation to the device in one of the various degrees of freedom, as noted above. Moreover, the device may include multiple functional elements 106, such as at least two of a light, laser, and a camera element, or any one of the other functional elements noted above. The light or fiber optic light guides may also be fixed to any one of the housings or incorporated into the camera element. In one embodiment, the multiple instruments may be controlled consistently with each other. For example, a light may be controlled in the various degrees of freedom to illuminate the site consistent with the movement of the camera element. In one embodiment, the insertable device 100 includes a plurality of shuttles 135, one shuttle 135 including a camera element and at least one shuttle 135 which includes a functional element, such as a light, a laser, etc., thereon.

As noted above, the present invention may be temporarily placed into a luminal structure for minimal access procedures to obviate some or all of the drawbacks of probe-like instruments, such as endoscopes, graspers, dissectors, etc., that pivot at the access opening of the luminal structure. Probe-like instruments are generally slender instruments intended to be inserted into the luminal structure for use in minimal access procedures. The present invention may also be used in connection or combined with such instruments to provide additional functionality thereto. For example, a grasper or an ultrasound dissector may be equipped with one or more functional elements, such as a camera element, moveably connected thereto, to similarly retract into and out of from the probe. In this instance, the body or a tubular section of the probe-like instrument forms the first housing from which the camera element may be retracted, for insertion into the luminal structure and extracted therefrom to provide an image of the site of interest. Any probe-like instrument may similarly be equipped with one or more functional elements, such as a circular stapler, to perform e.g., anastomosis. One of or more of the functional elements discussed above may be combined with any type of slender instrument to provide instruments with multiple functions thereby limiting the number of access openings to access the site of interest.

Referring to FIGS. 7-12, in one embodiment, the device 100 includes at least one electrical circuit that electrically and/or communicatively couples the functional element 106, the shuttle 135, an actuating device 108, 190, or a combination thereof, with a driving device 220. The electrical circuit generally includes at least one wire 202 disposed within the first housing 102 and at least one contact 204 associated with the shuttle 135. The wire 202 generally receives and/or communicates power, energy, sensor, video, or drive signals, as discussed above, from the cable 210 that interfaces with the driving device 220. The wire 202 may also receive or communicate with a local communication unit located on the device 100 (not shown), which communicates wirelessly with a corresponding communication unit 214 associated with the driving device 220, and with a local power supply also located on the device 100, to generally provide wireless control of the insertable device 100. The wire 202 is generally disposed along at least a portion of the length of the first housing 102 essentially parallel or inline with the elongated axis of the device 100 so that the contact 204 associated with the shuttle 135 remains in contact the wire 202 as the shuttle 135 translates within the first housing 102. A wire 202 is generally any electrically conductive structure that may be so disposed, such as a wire having a circular, square, or a rectangular cross section, such as in the form of a conductive film, etc. The wire 202 may be adhered to the first housing 102 or integrated therein.

The contact 204 generally connects an actuating device 108, 190 or a functional element 106 associated with the shuttle 135 with the wire 202, e.g., using wire 208, while the shuttle 135 translates along within the first housing 102, preferably for the full range of motion of the shuttle 135. Various types of contacts may be used in this respect. The contact 204 may, for example, include a bearing, such as a ball bearing, disposed in a recess 206, which bearing contacts wire 202 and wire 208 thereby establishing continuity between the cable 210 and the actuating device 108, 190 or functional element 104. The contact 204 may be biased toward the wire 202 to maintain continuous contact with the wire 202 as the shuttle 135 translates within the first housing 102. Bias may be maintained with a spring that forces the bearing toward the wire 202. The spring is preferably electrically conductive to maintain the desired continuity in the circuit.

Referring to FIGS. 11 and 12, the device 100 may include a plurality of electrical circuits. For instance, an electrical circuit may be used to conduct a drive signal to the actuating device 108, 190. An electrical circuit may also be used, depending on the type of functional element, to conduct energy or communicate image or other data to or from the functional element 106. For example, an electrical circuit or channel may communicate image data from a camera element or an ultrasound probe. Similarly, the electrical circuit may conduct energy for an ultrasonic dissector or any other type of effector and receive data therefrom. In instances where functional elements may interfere with each other, such as a camera element and an ultrasound probe, the functional elements preferably operate at different frequencies or include some other means for limiting interference. The device 100 may also include a sensor, such as an oxygen sensor or oximeters, a stress/strain sensor, a temperature sensor, a pressure sensor, haptic feedback devices, etc., disposed on the functional element 106 or elsewhere on the device 100, to obtain relevant data from the site of interest. In this instance, the device 100 may include a circuit or channel to communicate sensor data from the sensor to the driving device 220. Haptic feedback devices generally provide the user with feedback regarding feel, usually by generating resistive forces in input device. When the driving device includes imaging, sensor, and effector elements or subsystems, the device integrates control of all of these systems.

The electrical circuits may be disposed longitudinally at various locations in the first housing 102 as dictated by the size of the device 100. That is, for relatively large devices 100, all of the electrical circuits may be disposed in a localized area or areas of the first housing 100 without limitation. In contrast, for smaller devices 100 the electrical circuits may be spaced sufficiently apart around the perimeter of the first housing 102 to accommodate as many circuits as desired. The contacts 204 may also be longitudinally spaced on the shuttle 135 as shown in FIG. 11 and FIG. 12 to allow the wires 202 to be spaced closer together to accommodate more wires 202, and thus more circuits or channels, than may otherwise be available with all of the contacts 204 on the same plane.

The actuating elements 108, 190 or the functional elements 106 may also share electrical circuits or portions thereof. For example, the actuating elements disposed on the shuttles 135 as well as those producing translational movement may share a common ground. In this instance, one of the wires 202 will serve as a ground bus for a plurality of actuating elements 108, 190. A plurality of wires 202 may also serve as a communication bus for the functional elements 106. For example, a plurality of camera elements, oxygen sensors, stress/strain sensors, pressure sensors, temperature sensors, etc., or a combination thereof, may communicate data with a common set of wires 202. The data communicated from these data acquisition devices may also include a data string, such as a header, or some other means that associates the data with the particular type of capturing device. For example, image data may be preceded with a data string that identifies the data that follows as image data. Where a plurality of camera elements communicate over the data bus, the data string or header may also associate the image data that follows with a particular camera element.

Figure 7:
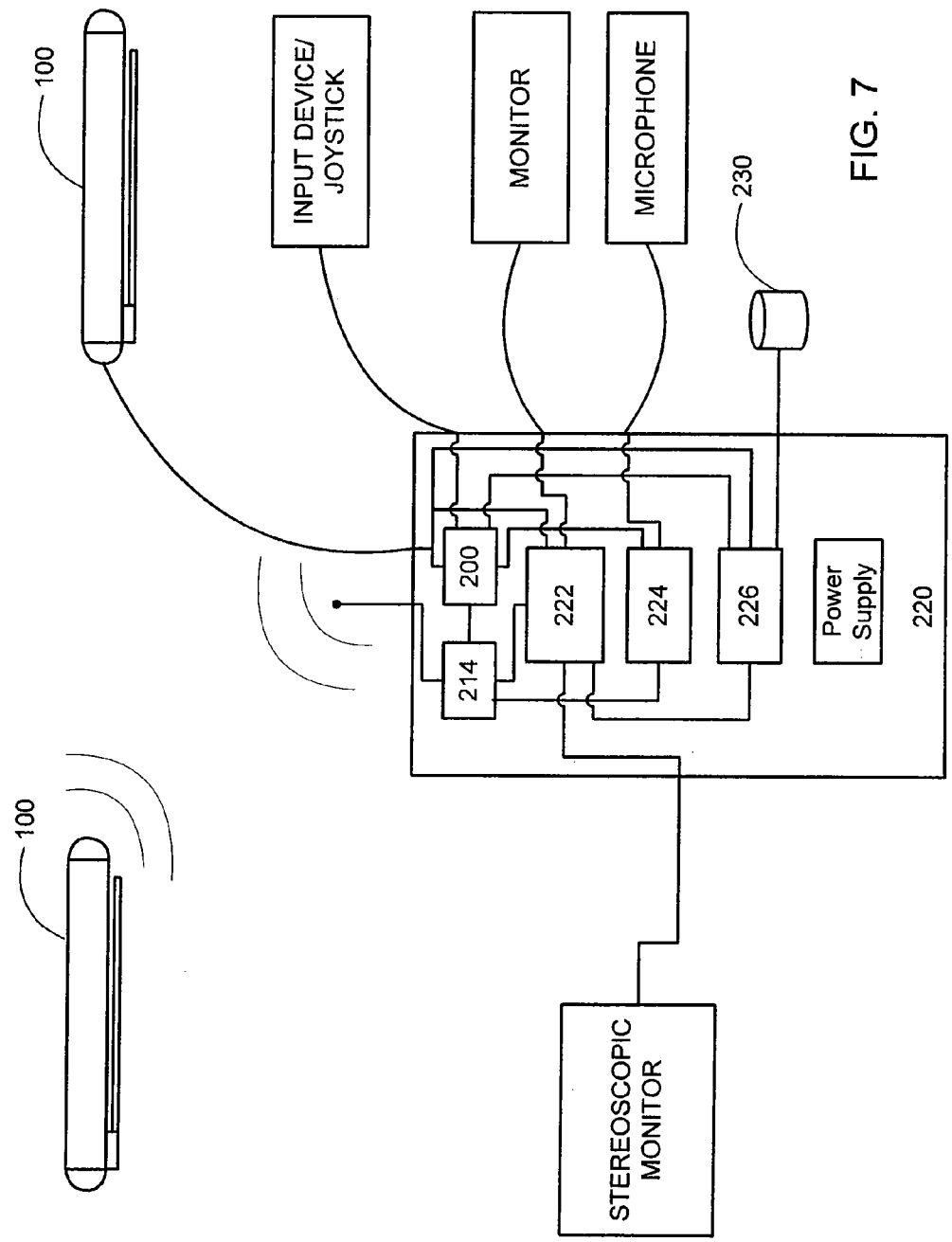
FIG. 7 is a diagram of a minimal access system according to one embodiment of the present invention.

Referring to FIG. 7, a minimal access system, according to one embodiment, includes at least one insertable device 100 or a plurality of insertable devices 100 communicatively coupled to a driving device 220. The driving device 220 is generally a device, which provides the driving signal or signals to produce the desired functionality with the insertable device 100, such as movement in the relevant degrees of freedom of motion, imaging, provide power or energy for cauterizing, coagulation, ablation, for actuating graspers, scissors, etc. The driving device 220 as well as the other components discussed herein may be implemented in hardware, software, or a combination thereof. Although the driving device 220 may be discussed by way of example in relation to certain modules or components, it is understood that the functionality of the driving device 220 may be accomplished with a variety of hardware and software components and is thus not limited thereto.

In one embodiment, the driving device 220 includes at least one controller 200 to drive at least one motor associated with the device 100 and to reproduce the images of the site of interest. The controller 200 may consist of a plurality of controllers, such as a motor controller for each of the actuating devices incorporated into the device 100, a camera controller for each of the camera elements, and specific controllers for each of the other types of functional elements. The motor controllers generally provide the drive signal to control the operation of the actuating elements and the camera controllers provide the signal to control the functions of the camera based on signals from, e.g., an input device, a voice recognition module 224, an image tracking module 226, etc. The driving device 220 may also include a power supply that provides the power for the actuating elements electrically connected to the driving device 220 and the functional elements communicatively connected to the driving device 220, as well as the components of the driving device 220. The controller or controllers may operate the elements of the device 100 based at least initially on a signal from an input device, such as a joystick and/or from a component that provides a signal for automatically controlling the elements of the device 100. In one embodiment, the system includes a plurality of insertable devices 100 with each of the devices 100 providing a different functionality, such as one of imaging, light, coagulation, and ablation.

The driving device 220 may also include an image processor/display adaptor 222, which receives image data or other types of acquired data from at least one insertable device 100 and converts image data received from the camera elements or sensors into a signal suitable for displaying the image on a monitor, such as a CRT display, an LCD display, stereoscopic goggles, etc. The image processor generally receives image data from the camera elements and produces a video image of the site of interest for continuous video display. With other types of data acquisition elements, the system may convert the signal received from these elements into a numerical or graphical representation of the signal for display. For instance, the system may convert a signal from a pressure sensor into a numerical value. The image processor may also process the image data for other purposes, such as to extract data from the image data. The extracted data, may represent an object or a portion of the object in the field of view, which may be used to track the object as discussed below.

In one embodiment, the system provides hybrid control, which allows the user to control movement with regard to some of the degrees of freedom of the device 100 while the system autonomously controls movement with regard to the remaining degrees of freedom. For example, the system may be adapted to autonomously control camera movement in the first and second degrees of freedom 130, 140 in order to keep a user-identified object in view, while the user controls camera movement along the third degree of freedom to provide images from different orientations/perspectives. In one embodiment, the autonomous system maintains the user identified object, such as an organ, in view while the user orients at least one camera element. This may be accomplished with a constraint-based sensor planning system that can associate viewpoints of modeled objects. The planning system generally incorporates constraints on viewpoint visibility, depth-of-field, and image resolution to plan correct viewing parameters and positions. This aspect is particularly beneficial when multiple camera insertable devices are in use to provide surgeons with a choice of potential viewpoints and to provide stereoscopic imaging.

The system may also independently track user-identified objects to maintain such objects in view when the objects move in the site of interest or more particularly in the image field. For example, the system may track the movement of organs or instruments in a subject's abdominal cavity and control the camera element to maintain the organ or instrument in view during a minimal access procedure or a portion thereof. This may be accomplished with a tracking module 226, which receives a first set of image data of the site of interest and instruction regarding an object or objects to be tracked, which object or objects are represented in the first set of image data. A set of image data generally includes data sufficient to identify an object in the field of view. The set of image data may include sufficient data to produce an image or frame of a video or a subset of such data. The user defined targeting instructions may be received with a pointing device that allows the user to select an object or point on a graphic display of the site of interest. The pointing device may be a mouse, a joystick, a stylus, a touch screen display, etc. The tracking module 226 receives a subsequent set of image data and tracks movement therein of the user-identified object based on differences between the first set of image data and the subsequent set of data. Accordingly, movement may be tracked in real-time based on a comparison of contiguous and/or sequential image data sets or frames obtained at different times. The image data sets may be stored in a data store 230 associated with the tracking module for tracking or for reproduction at a later time.

Figure 14:
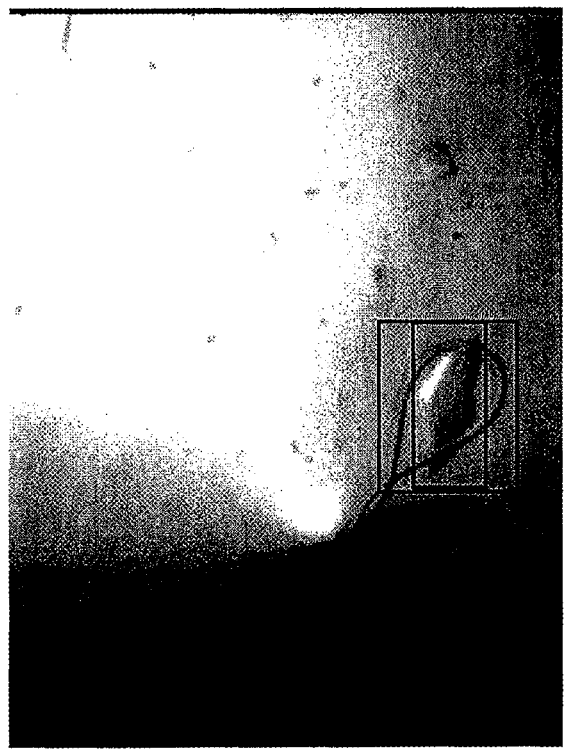
FIG. 14 is an image of a protein crystal and grasping loop in a subsequent sequence of a video image used to track the movement of the grasping loop in the video image.
Figure 13:
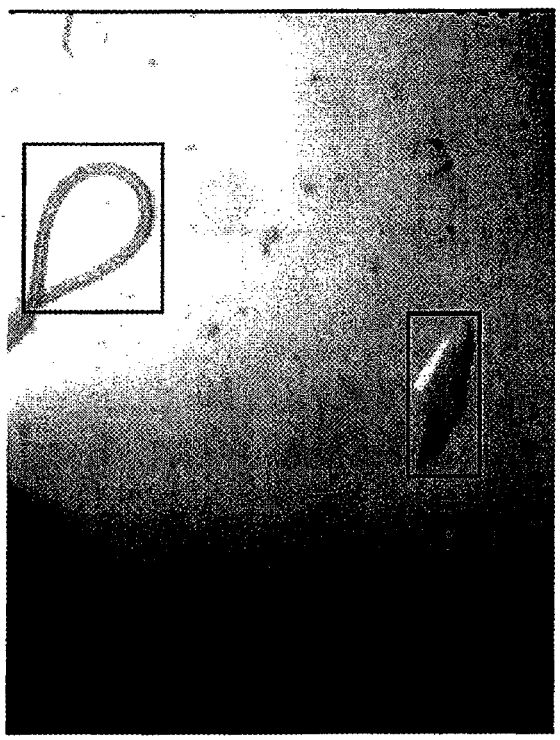
FIG. 13 is an image of a protein crystal and a grasping loop in a beginning sequence of a video image used to track the movement of the grasping loop in the video image.

The tracking module 226 may operate on many different imaging cues, such as gray-level regions, geometric features, motion, fiducial markers, etc. In one embodiment, image processing is used to identify a target based on its RGB color components. In this respect, any movement of the target may be tracked by following the target's RGB color components. The tracking algorithms discussed herein have been applied to track protein crystals and a grasping loop in real time as shown in FIGS. 13-14. FIG. 13 shows the beginning sequence and FIG. 14 shows the tracking convergence as the grasping loop is placed under the crystal to pick it up.

As noted above, the tracking module may track one or more features, instruments, or organs and provide information to the controller 200 in order to maintain the targeted object in view. This may be accomplished in a variety of ways. In one embodiment, once the targeted object is identified, the camera element may be moved in a first, second, or third degree of freedom, or a combination thereof, to pan and tilt the camera as needed to keep the target centered in the image or at any other point in the image. Computer control algorithms may be used to pan and tilt the camera elements. For example, a vertical or horizontal error measured in image pixels from the image center may be used to control tilt and pan, respectively, where the velocity is proportional to the rate of the vertical/horizontal pixel errors. The control signals may generally be updated periodically, such as 30 times per second, for real-time control. The tracking module 226 may also provide a signal to the controller 200 to automatically and independently verge a plurality of camera elements on tracked objects to allow stereoscopic imaging of the object in 3D. A plurality of objects may also be tracked independently and a plurality of camera element may each be controlled separately to provide a range of viewpoints to a surgeon while maintaining each of the tracked objects in the field of view. This is particularly useful with minimal access procedures that involve multiple organs/instruments.

Although the present invention has been described in particular detail with regard to imaging platforms, which include one or more camera elements, the present invention may generally serve as a basis for other data acquisition platforms or effector platforms. To facilitate remote, open or closed loop, or hybrid control with regard to effector platforms, the functional elements may include sensors, such as stress/strain, ultrasound, haptic, RF, etc., that provide feedback for use in tracking and actuating the effector type of functional elements. Additional data input with the addition of various sensors on the effectors may further guide decision making by the surgeon with input from the computer. For example, sensors that may be used include ultrasound probes, oximeters, or haptic feedback devices to measure the pressure required to affect a task (conceptually, the equivalent of tactile sensation).

The system may further be adapted to perform open loop position control of the one or two functional elements in the relevant degrees of freedom, interface the open loop control to the surgeon through either voice activation or an input device, such as a joystick, an alphanumeric keypad, etc., produce a video image of the site, track moving structures within the body, and/or create stereo images in real-time based on automatic vergence algorithms. Stereo images may be displayed on head-mounted stereoscopic goggles for immersive 3D stereo imaging.

The driving device 220 generally provides control remote from the insertable device 100, e.g., the driving device 220 is located exterior to the body whereas the insertable device 100 may be implanted to provide the relevant functionality with respect to minimal access procedures. The driving device 220 may interface with the device 100 with cables, such as a cable 2 m long and 1-12 mm in diameter. The cable generally includes a plurality of wires that carry power, energy, video, and/or the drive signal to control the elements of the device 100. Alternatively, the video and/or the drive signal may be wirelessly transmitted to the device to reduce the number of wires necessary to operate the device 100. In this instance, the driving device 220 includes a communication module 214 that allows devices 100 with corresponding communication modules to communicate with each other. Power may also be provided with a battery within the driving device 100 to eliminate cabling altogether. For extended use the battery may be charged or maintained with wireless energy transducers.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A system for minimally-invasive surgical procedures within an operative space of a patient, the system comprising:
   a) at least one device, insertable into the operative space, the insertable device comprising:
      i) an elongate body having a longitudinal first axis, adapted and configured so as to be fully insertable into the operative space, the body comprising a first body portion, substantially coaxial with the first axis, and a second body portion substantially coaxial with the first axis, axially rotatably connected to the first body portion, permitting relative rotation between the first and second body portions about the first axis;
      ii) a first actuator provided in the body, adapted and configured to effect rotational movement of the first body portion with respect to the second body portion;
      iii) a camera mounted to the first body portion for rotation about a second axis, substantially transverse to the first axis; and
      iv) a second actuator provided in the body, adapted and configured to effect rotation of the camera about the second axis; and
   b) a driving device communicatively connected to the insertable device, the driving device comprising:
      i) at least one controller that provides a driving signal to at least one of the first and second actuators to control movement of the camera; and
      ii) an image tracking module for tracking movement of at least one object in a field of view of the camera, wherein the controller controls movement of the camera based on signals from the image tracking module such that the camera is adapted and configured to move based on the movement of the at least one object.

2. The system of claim 1, wherein the controller controls movement of the camera so as to maintain the at least one object within a field of view of the camera.

3. The system of claim 1, wherein the image tracking module is adapted and configured to track movement of a user-identified object.

4. The system of claim 1, wherein the tracking module:
   receives a first set of image data of a site of interest including a representation of the at least one object;
   receives tracking instruction regarding the at least one object;
   receives a second set of image data; and
   tracks movement of the at least one object based on differences between the first set of image data and the second set of image data.

5. The system of claim 4, wherein the tracking module tracks the at least one object based on RGB color components, color centroid, gray-level regions, geometric features, texture, edges, corners, curvature, size, orientation, area, motion, or fiducial markers, or by optical flow, automatic vergence, triangulation or probability algorithms.

6. The system of claim 1, wherein the camera is adapted and configured for repeated retraction into and extraction from the body of the insertable device by way of control of at least one of the first and second actuators.

7. The system of claim 1, wherein the controller autonomously controls movement of the camera based on signals from the image tracking module in at least one degree of freedom by way of control of one or more of the first and second actuators.

8. The system of claim 7, wherein a user controls movement of the camera in at least one other degree of freedom by way of control of one or more of the first and second actuators.

9. A system for minimally-invasive surgical procedures within an operative space of a patient, the system comprising:
a) at least one device, insertable into the operative space, the at least one insertable device comprising:
   i) an elongate body having a longitudinal first axis, adapted and configured so as to be fully insertable into the operative space, the body comprising a first body portion, substantially coaxial with the first axis, and a second body portion substantially coaxial with the first axis, axially rotatably connected to the first body portion, permitting relative rotation between the first and second body portions about the first axis;
   ii) a first actuator provided in the body, adapted and configured to effect rotational movement of the first body portion with respect to the second body portion;
   iii) a first functional element comprising a first camera mounted to the first body portion for rotation about a second axis, substantially transverse to the first axis; and
   iv) a second actuator provided in the body, adapted and configured to effect rotation of the first functional element about the second axis; and
b) a driving device communicatively connected to the at least one insertable device, the driving device comprising:
   i) at least one controller that provides a driving signal to at least one of the first and second actuators to control movement of the first functional element; and
   ii) an image tracking module for tracking movement of at least one object in a field of view of the first camera, wherein the controller controls movement of the first functional element based on signals from the image tracking module such that the first functional element is adapted and configured to move based on the movement of the at least one object.

10. The system of claim 9, the insertable device further comprising:
a) a third body portion substantially coaxial with the first axis, axially rotatably connected to the second body portion, permitting relative rotation between the second and third body portions about the first axis;
b) a third actuator provided in the body, adapted and configured to effect rotational movement of the third body portion with respect to the second body portion; and
c) a second functional element mounted to the third body portion for rotation about a third axis, substantially transverse to the first axis.

11. The system of claim 10,
a) wherein the second functional element is a second camera;
b) wherein the image tracking module is adapted and configured for tracking a plurality of objects in respective fields of view of each of the first and second cameras; and
c) wherein the controller controls movement of each of the first and second cameras independently from one another based on signals from the image tracking module.

12. The system of claim 10,
a) wherein the second functional element is a second camera;
b) wherein the image tracking module is adapted and configured for tracking a single object in respective fields of view of each of the first and second cameras; and
c) wherein the controller controls movement of each of the first and second cameras based on signals from the image tracking module such that the first and second cameras converge on the single object for stereoscopic imaging of the single object.

13. The system of claim 10, wherein the second functional element is biological sensor.

14. The system of claim 13, wherein the second functional element is an oximeter.

15. The system of claim 13, wherein the driving device additionally controls the biological sensor.

16. The system of claim 10, wherein the second functional element is a surgical effector.

17. The system of claim 16, wherein the second functional element is a light source.

18. The system of claim 16, wherein the second functional element is a grasper.

19. The system of claim 16, wherein the driving device additionally controls the surgical effector.

20. A system for minimally-invasive surgical procedures within an operative space of a patient, the system comprising:
a) at least one device, insertable into the operative space, the at least one insertable device comprising: i) an elongate body having a longitudinal first axis, adapted and configured so as to be fully insertable into the operative space, the body comprising a first body portion, substantially coaxial with the first axis, and a second body portion substantially coaxial with the first axis, axially rotatably connected to the first body portion, permitting relative rotation between the first and second body portions about the first axis; ii) a first actuator provided in the body, adapted and configured to effect rotational movement of the first body portion with respect to the second body portion; iii) a camera mounted to the first body portion for rotation about a second axis, substantially transverse to the first axis; and iv) a second actuator provided in the body, adapted and configured to effect rotation of the camera about the second axis; and b) a driving device communicatively connected to the at least one device, the driving device comprising: i) at least one controller for providing a driving signal to the first and second actuators thereby controlling movement of the camera; and ii) an image tracking module for tracking movement of an object in a field of view of the camera, wherein the controller controls movement of the camera based on a signal from the image tracking module for maintaining the object in the field of view of the camera, such that the camera is adapted and configured to move based on movement of the object.

* * * * *